(12) United States Patent
Murray

(10) Patent No.: US 10,252,259 B2
(45) Date of Patent: Apr. 9, 2019

(54) ION EXCHANGE RESINS SELECTIVE FOR THE COMPLEXATION OF UNIVALENT ANIONS IN AQUEOUS SOLUTIONS

(71) Applicant: TechSource, Inc., Los Alamos, NM (US)

(72) Inventor: George M Murray, Tullahoma, TN (US)

(73) Assignee: TechSource, Inc., Los Alamos, NM (US)

(*) Notice: Subject to any disclaimer, the term of this patent is extended or adjusted under 35 U.S.C. 154(b) by 27 days.

(21) Appl. No.: 15/172,095

(22) Filed: Jun. 2, 2016

(65) Prior Publication Data

US 2016/0354770 A1 Dec. 8, 2016

Related U.S. Application Data

(60) Provisional application No. 62/169,630, filed on Jun. 2, 2015.

(51) Int. Cl.

| | |
|---|---|
| *B01J 39/20* | (2006.01) |
| *G01N 21/64* | (2006.01) |
| *B01J 45/00* | (2006.01) |
| *B01D 15/36* | (2006.01) |
| *C02F 1/42* | (2006.01) |
| *B01D 15/10* | (2006.01) |

(Continued)

(52) U.S. Cl.
CPC .............. *B01J 39/20* (2013.01); *B01D 15/10* (2013.01); *B01D 15/361* (2013.01); *B01D 15/363* (2013.01); *B01J 41/05* (2017.01); *B01J 41/14* (2013.01); *B01J 45/00* (2013.01); *C02F 1/42* (2013.01); *C22B 3/04* (2013.01); *C22B 3/42* (2013.01); *C22B 11/04* (2013.01); *G01N 21/64* (2013.01); *C02F 1/285* (2013.01); *C02F 2001/422* (2013.01); *C02F 2101/12* (2013.01); *C02F 2101/20* (2013.01);

(Continued)

(58) Field of Classification Search
None
See application file for complete search history.

(56) References Cited

U.S. PATENT DOCUMENTS

| | | | |
|---|---|---|---|
| 5,814,671 A | 9/1998 | Murray | |
| 6,780,323 B2 | 8/2004 | Murray | |

(Continued)

FOREIGN PATENT DOCUMENTS

WO WO0177672 A2 10/2001

OTHER PUBLICATIONS

Helfferich, "Ion Exchange", 1995, 151-200.

(Continued)

*Primary Examiner* — Betty J Forman
(74) *Attorney, Agent, or Firm* — Peacock Law P.C.; Philip D. Askenazy; Deborah A. Peacock

(57) ABSTRACT

Ion exchange resin macroporous beads for the highly selective extraction of univalent anions from aqueous solutions. A specific example is the removal of dicyanoaurate and dicyanoargentate from cyanide leach solutions and tailings. The beads have a maximum number of ligands specific for the desired univalent anion, while maintaining sufficient separation to minimize binding of polyvalent ions. The beads are prepared using a functionalized monomer with the use of a specifically tuned coordinator. The beads can be used as a sensor for detecting the amount of anions captured when interrogated by an appropriate light source.

15 Claims, 2 Drawing Sheets

(51) Int. Cl.
*C22B 3/00* (2006.01)
*C22B 3/04* (2006.01)
*C22B 3/42* (2006.01)
*B01J 41/14* (2006.01)
*B01J 41/05* (2017.01)
*C02F 103/10* (2006.01)
*C02F 103/00* (2006.01)
*C02F 1/28* (2006.01)
*C02F 101/12* (2006.01)
*C02F 101/20* (2006.01)
*C02F 103/06* (2006.01)
*C02F 103/36* (2006.01)

(52) U.S. Cl.
CPC .... *C02F 2103/007* (2013.01); *C02F 2103/06* (2013.01); *C02F 2103/10* (2013.01); *C02F 2103/365* (2013.01); *C02F 2209/003* (2013.01); *Y02P 10/234* (2015.11)

(56) References Cited

U.S. PATENT DOCUMENTS

| | | | |
|---|---|---|---|
| 7,279,096 B2 | 10/2007 | Murray | |
| 7,476,316 B2 | 1/2009 | Southard | |
| 8,058,208 B2 | 11/2011 | Murray et al. | |
| 8,241,575 B2 | 8/2012 | Murray et al. | |
| 8,591,842 B2 | 11/2013 | Murray et al. | |
| 2007/0090058 A1* | 4/2007 | Southard | B01J 20/26 210/727 |
| 2008/0144002 A1 | 6/2008 | Murray et al. | |
| 2012/0288426 A1* | 11/2012 | Rezkallah | B01J 39/26 423/179.5 |

OTHER PUBLICATIONS

Moriuchi, et al., "Poly-L-lysine-induced Self-association and Luminescence of Dicyanoaurate(I)", Chem. Lett. vol. 39, 2010, 841-843.
Dobbs, et al., "Electrodeposition of Silver Particles and Gold Nanoparticles from Ionic Liquid-Crystal Precursors", Angew. Chem. 2006, 118, 4285-4288, 2006.
Dam, Hoang Anh, et al., "Selective Copper(II) Sorption Behavior of Surface-Imprinted Core-Shell-Type Polymethacrylate Microspheres", Ind. Eng. Chem. Res. 2009, 48, 5679-5685, 2009.
Kimaro, Anael, et al., "Synthesis and Characterization of Molecularly Imprinted Uranyl Ion Exchange Resins", Separation Science and Technology, 40: 2035-2052, 2005, 2005.
Murray, George M., et al., "Molecularly Imprinted Ionomers", Mat. Res. Soc. Symp. Proc. vol. 723 2002 Materials Research Society, 2002.

* cited by examiner

ION EXCHANGE RESINS SELECTIVE FOR THE COMPLEXATION OF UNIVALENT ANIONS IN AQUEOUS SOLUTIONS

CROSS-REFERENCE TO RELATED APPLICATIONS

This application claims priority to and the benefit of filing of U.S. Provisional Patent Application Ser. No. 62/169,630, entitled "Ion Exchange Resins Selective for the Complexation of Gold and Silver in Cyanide Leach Solutions", filed on Jun. 2, 2015, the specification and claims of which are incorporated herein by reference.

BACKGROUND OF THE INVENTION

Field of the Invention (Technical Field)

The present invention relates to a technology developed for the highly selective extraction of univalent species from aqueous solutions. The technology is preferably expressed in terms of macroreticular (macroporous), strong base, ion exchange resin (IER) beads that have been specifically prepared for the complexation of univalent anions. The beads are preferably prepared using a functionalized monomer or in a conventional manner in terms of the order of steps, but with precisely controlled parameters and the use of a specifically tuned coordinator. The beads can also sense the degree of loading by being interrogated optically, resulting in a characteristic luminesce.

Background Art

Note that the following discussion may refer to a number of publications and references. Discussion of such publications herein is given for more complete background of the scientific principles and is not to be construed as an admission that such publications are prior art for patentability determination purposes.

Precious metals are typically removed from ore using cyanide solutions that in the presence of atmospheric oxygen dissolve the metals to make soluble cyanide metal complexes. Some base metals, such as copper, mercury, lead and iron, are also dissolved and form cyanide complexes as well. The dissolved metals are then adsorbed on a material. The materials employed are selective in the adsorption process, but the current materials employed also adsorb base metal cyanide complexes. Many univalent ions have toxic properties or are economically useful. However, commercial ion exchange resins are more selective for ions with higher charges and are not suitable for the selective complexation of univalent species.

Carbon or activated charcoal is one of the materials used to adsorb precious metal cyanide complexes from aqueous solutions. Activated carbon is inexpensive to produce, absorbs dicyanoaurate readily, has a large capacity, and may be regenerated. Unfortunately, activated carbon also has a high affinity for mercury (II) tetracyanide, and under some conditions mercury (II) tetracyanide may actually displace dicyanoaurate from the activated carbon. Like dicyanoargentate, mercury (II) tetracyanide desorbs with dicyanoaurate when eluted from the activated carbon. Mercury (II) tetracyanide is also reduced to elemental mercury during the electrowinning process that isolates metallic gold. The mercury can be removed from the impure gold by thermal processes, but some is inevitably lost to the atmosphere. It would be preferable to use a sorbent that selectively removes gold and silver from the leachates to avoid environmental concerns. Furthermore, the elution process is not incomplete for activated carbon and some mercury remains on the activated carbon. During thermal reactivation of the activated carbon, the mercury is reduced to mercury metal that volatilizes and escapes into the atmosphere. The reactivation step is unavoidable as activated carbon also absorbs organic matter that fouls and reduces its sorption capacity. Thus the reuse of activated charcoal is limited and losses are significant.

Another method for removal of gold from cyanide leach solutions involves anion exchange resins. Both weak base and strong base anion exchange resins have been employed. Ion exchange should also allow better recycling of cyanide. Certain specialty resins have been applied to sequestration of gold and silver. The issue with existing IERs is a lack of specificity, due to the method used to prepare anion exchange resins. High capacity is sought by applying a poorly controlled high degree of functionalization. This results in close proximity of binding sites resulting in a higher affinity for species with multiple charges. This process also makes these resins unlikely to have selectivity for any univalent species.

Ion imprinting can be used to manufacture beads with a higher selectivity than commercial beads. However, the coordination sites are typically aggregated in this process, which increases cooperative effects leading to lower selectivity for target ions and increasing selectivity for polyvalent ions. In addition, the manufacturing method is expensive and hazardous, requiring the use of precious metals and cyanide. The resulting beads always have residual precious metal cyanide complexes as well.

Selectivity of conventional strong base anion exchange resins is usually explained in terms of the size of the hydrated ion, the charge on the ion and sieving effects (large ions). Specific associations with the ionogenic site are usually overwhelmed by physical parameters. Thus the counter ion having a higher valence, having the smallest hydrated volume (unless the crosslinking is so high that only an unsolvated ion may penetrate), of greater polarizability, or that is least involved in complexation will be preferred. These properties are a result of the degree of functionalization and the hydrophobicity of the binding site.

Anion association can also be understood as a function of the quaternizing agent (hydrophobicity) and the loading of the ionogenic sites. The preference for ions of higher valence can be addressed by controlling the degree of functionalization and the distribution of sites. Conventional strong base anion exchange resins are functionalized as heavily as possible using a hydrophilic quaternizing agent. Using a less hydrophilic quaternizing agent can change the hydrophilicity. This combined with higher degrees of crosslinking and greater sieving effects are particularly important when building selectivity for complex species.

SUMMARY OF THE INVENTION (DISCLOSURE OF THE INVENTION)

The present invention is a macroporous ion exchange resin polymer bead comprising a plurality of ligands selective for a specific univalent ion, the ligands co-polymerized with a non-complexing monomer and a crosslinker, wherein each ligand comprises a coordination site supplying the appropriate charge for the univalent ion and wherein the ligands are sufficiently separated to minimize binding of polyvalent ions to the bead. The monomer optionally comprises styrene and the crosslinker optionally comprises divinyl benzene. The bead preferably does not comprise the univalent ion. The ligand is preferably cationic and preferably monodentate. There is preferably a number of ligands to substantially maximize a binding capacity of the bead to the univalent ion while maintaining spatial separation to minimize cooperative effects between ligands. The ligand is preferably selected from the group consisting of cationic oxygen containing heterocyclics, cationic nitrogen containing heterocyclics, cationic sulfur containing heterocyclics, cationic phosphorous containing heterocyclics, ammonium salts, phosphonium salts, acylinium salts, metallocenium salts, amidinium salts, imminium salts, trityl salts, 4-vinyl-benzyl-N,N,N-tripentylammonium, 4-vinylbenzyl-N,N-dimethyl-N-hexylammonium, N,N-dimethyl N-heptylammonium, and 4-vinylbenzyl-N,N-dimethyl-N-decylammonium. The univalent ion is preferably selected from the group consisting of monatomic univalent anions, polyatomic univalent anions, halides, fluoride, chloride, bromide, iodide, univalent oxyanions, perbromate, periodate, permanganate, pertechnetate, nitrite, nitrate, perchlorate; cyanide, cyanate, thiocyanate; organic anions, benzoate, acetate, precious metal cyanide complexes, dicyanoaurate, and dicyanoargentate. The univalent ion is preferably luminescent.

The present invention is also a method for extracting univalent ions from a liquid, the method comprising flowing the liquid past a plurality of the beads of claim 1, maintaining contact between the liquid and the beads sufficiently long for the liquid to substantially penetrate the beads, and binding the univalent ions to the ligands. The plurality of beads is preferably in the form of a bed or column. The liquid optionally comprises an aqueous solution, potable water, produced water, mine effluent, mine waste, industrial effluent, a settling pond, an evaporation pond, a contaminated natural body of water, or an underground water table. The method optionally further comprises shining light on the beads, luminescing the univalent ions bound to the beads, and measuring a characteristic, such as intensity or wavelength, of the luminescence. The method preferably comprises determining when the plurality of beads is saturated with bound univalent ions. The plurality of beads preferably have an average size between approximately 50 microns and approximately 1.5 mm, and more preferably between approximately 300 microns and approximately 1000 microns.

The present invention is also a method of making a macroporous ion exchange resin polymer bead, the method comprising preparing a ligand selective for a univalent ion, preparing a copolymerizable organic soluble complex comprising the ligand, a non-complexing monomer, and a crosslinker, and suspension polymerizing the complex to form a macroporous polymer bead comprising the ligand co-polymerized with the monomer and the crosslinker, the ligands sufficiently separated to minimize binding of polyvalent ions to the bead. The monomer optionally comprises styrene and the crosslinker optionally comprises divinyl benzene. The method is preferably performed without imprinting of the univalent ion. The organic soluble complex preferably comprises a thixotropic agent. The method preferably comprises agitating the organic soluble complex prior to or after adding it to a polymerization reaction vessel. Agitating the complex preferably forms droplets of the monomer.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating certain embodiments of the invention and are not to be construed as limiting the invention. In the drawings.

DETAILED DESCRIPTION OF EMBODIMENTS OF THE INVENTION

Figure 1:
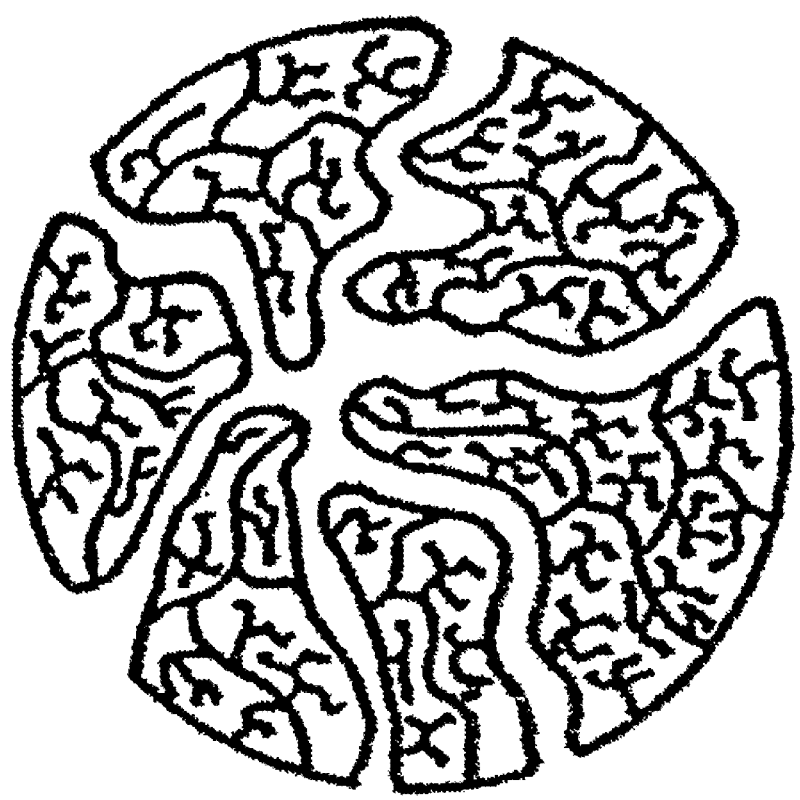
FIG. 1 is a graphic illustration of the polymer matrix of the cross-linked polymer bead having a macroporous structure according to the present invention.

In accordance with one embodiment of the present invention, a strong base anion exchange resin is functionalized in a controlled manner with a coordinator selective for univalent anions, including monatomic and polyatomic univalent anions. These include, but are not limited to: halides, such as fluoride, chloride, bromide and iodide; univalent oxyanions such as perbromate, periodate, permanganate, pertechnetate, nitrite and nitrate; cyanide, cyanate and thiocyanate; and organic anions such as benzoate and acetate.

In accordance with a second embodiment of the present invention, a method for detecting certain anions such as dicyanoaurate is provided comprising providing a contacting fluid containing a luminescent anion such as dicyanoaurate ion, and detecting the anions with a functionalized polymer sensor device possessing a porous structure having a plurality of complexing cavities therein. The complexing cavities preferably contain cationic ligands spatially oriented to selectively receive and bind dicyanoaurate ion to be detected and having operatively associated therewith a light source for generating excitation energy for the porous structure; and detecting luminescent energy generated by the porous structure upon excitation. Luminescence may also be provided by the beads themselves, in cases where the sorbed anion causes the intrinsic fluorescence of the polystyrene based beads to phosphoresce at a wavelength longer than the fluorescence wavelength, due to an external heavy atom effect. The energy detected is preferably proportional to the quantity sorbed.

Another embodiment of the present invention is a sequestering polymer comprising a plurality of complexing cationic ligands spatially distributed to selectively receive and bind univalent anions.

Embodiments of the present invention preferably use the technique of suspension polymerization for providing a selective binding site in an IER for specific anions. The transport of ions through the resins of the present invention is for separating, removing, or recovering the captured univalent ions, which is driven by environmental and medical concerns. By employing the device in the method of the present invention, the levels of the target ions in the device can be monitored to determine when the concentration of the target ions is sufficiently high such that the device needs to be recycled.

As used herein, the term "cationic" or "cation" refers to an ion that has a positive charge. This term can refer to polymeric compounds, such as ion exchange resins, that contain a positive charge.

As used herein, the term "anionic" or "anion" refers to an ion that has a negative charge.

As used herein, the term "ion" refers to an atom or group of chemically bonded atoms that have a positive or negative charge. This term includes all compounds even when referred to as polyatomic ions, coordinated complexes, ion exchange resins, etc. that have a negative or positive charge.

As used herein, the term "bind," "binding," "bond," "bonded," or "bonding" refers to the physical phenomenon of chemical species being held together by attraction of atoms to each other through sharing, as well as exchanging, of electrons or protons. This term includes bond types such as: ionic, coordinate, hydrogen bonds, covalent, polar covalent, or coordinate covalent. Other terms used for bonds such as banana bonds, aromatic bonds, or metallic bonds are also included within the meaning of this term.

As used herein, the term "light" refers to optical radiation, whether ultraviolet, visible or infrared. Suitable non-limiting examples of light sources include an argon laser, blue laser, tunable laser, light emitting diode (LED), combinations of two or more thereof, and the like.

As used herein, the term "macroporous" refers to particles that have a permanent porous structure even in the dry state.

As used herein, "reaction" is intended to cover single step and multi-step reactions, which can be direct reactions of reactants to products or may include one or more intermediate species, which can be stable or transient.

Suitable cationic ligands for the practice of the present invention include, but are not limited to, cationic oxygen containing heterocyclics, cationic nitrogen containing heterocyclics, cationic sulfur containing heterocyclics, cationic phosphorous containing heterocyclics, ammonium salts, phosphonium salts, acylinium salts, metallocenium salts, amidinium salts, imminium salts, trityl salts, or mixtures thereof. Representative examples of useful cationic ligands include 4-vinylbenzyl-N,N,N-tripentylammonium, 4-vinyl-benzyl-N,N-dimethyl-N-hexylammonium, N,N-dimethyl N-heptylammonium, or 4-vinylbenzyl-N,N-dimethyl-N-decylammonium.

The number of ligands needed to form a target cationic ligand complex depends on the functionality of the ligand and the target compound. At a minimum, the ligand is preferably able to bind the target compound and to be polymerized into a cationic polymer bead. The target compound and the ligand do not necessarily have to comprise multiple coordination sites capable of bonding. As one skilled in the art will readily appreciate, the ligand can be monodentate, bidentate or polydentate. A monodentate ligand can bond to only one coordination site. A bidentate ligand has the ability to bond to two separate coordination sites on a molecule simultaneously. Similarly, a polydentate ligand can simultaneously bind to multiple coordination sites. A ligand may contain more than one coordination site capable of bonding to a molecule but may nevertheless be a monodentate ligand if only one coordination site can bond to a molecule at any given moment. This may be due to stereochemistry of the ligand coordination sites. To selectively bind a univalent anion the monodentate ligands are preferably distributed far enough apart to avoid, prevent, or minimize binding multivalent ions.

A specific group of monomers may be used for synthesizing the beads in accordance with the principles of the present invention. Suitable non-limiting examples of monomers that can be used for preparing the beads of the present invention include: styrene, methyl styrene and divinylbenzene.

The choice of monomer and cross-linking agent is typically dictated by the chemical (hydrophilicity, chemical stability, degree of cross-linking, ability to graft to other surfaces, interactions with other molecules, etc.) and physical (porosity, morphology, mechanical stability, etc.) properties desired for the polymer. The amounts of ligand complex, monomer and crosslinking agents are preferably chosen to provide a crosslinked polymer exhibiting the desired structural integrity, porosity and hydrophilicity. The amounts can vary, depending on the specific nature/reactivities of the complex, monomer and crosslinking agent chosen as well as the specific application and environment in which the polymer will ultimately be employed. The relative amounts of each reactant can be varied to achieve desired concentrations of complexes in the polymer support structure. Typically, the amount of complex will be on the order of about 1 to about 10 percent of total monomer. The degree of crosslinking may, however, affect the amount of flux, i.e., a lower degree of crosslinking may provide a higher flux. The degree of cross-linking herein can range from about 5% to about 95%. Higher crosslinking provides greater mechanical strength.

The IER according to the present invention can be prepared by, for example, aqueous suspension polymerization of a copolymerizable mixture of an organic phase containing matrix monomer and cross-linker, and an aqueous phase containing at least one or more thixotropic agents. Suitable thixotropic agents employed herein are dependent on the type and amount of monomer employed and the suspending medium. The thixotropic agents typically used in conventional suspension polymerizations are advantageously employed herein. As one skilled in the art will readily appreciate, the thixotropic agents can also advantageously act as suspension agents during the suspension polymerization process. Representative examples of thixotropic agents include, but are not limited to, cellulose ethers such hydroxyethylcellulose, (commercially available under the trade name of "CELLOSIZE"), cross-linked polyacrylic acid known under the name of "CARBOPOL" polyvinyl alcohols known under the trade name of "RHODOVIOL", boric acid, gums such as xanthium gum and the like and mixtures thereof. The amount of thixotropic agents can influence the size of the IER (typically, the use of larger amounts of thixotropic agents often results in the formation of smaller IER particles). The amount of the thixotropic agents is generally from about 1.5 to about 5 weight percent, based on the weight of the monomers in the monomer mixture, and preferably from about 1.5 to about 2.5 weight percent, based on the weight of the monomers in the monomer mixture.

In the suspension polymerization procedure, the various phases can be thoroughly mixed separately prior to the start of the reaction and then added to the polymerization reaction vessel. While this mixing of the ingredients can be done in a vessel apart from the reaction vessel, the mixing can alternatively be conducted in the polymerization reaction vessel under an inert atmosphere, particularly where the monomers being employed are subjected to oxidation.

Polymerization typically proceeds at an elevated temperature, preferably above about 50° C. in the presence or absence of an initiator. Suitable initiators that can be used in the present invention include benzoyl peroxide, diacetylperoxide, and azo-bisisobutyronitrile (AIBN). The amount of initiator employed is within the range of about 0.005 to about 1.00% by weight, based on the weight of the monomer being polymerized. In the presence of an initiator, the temperature of reaction is maintained above that at which the initiator becomes active. Lower temperatures, e.g. about −30° C. to about 200° C., can be employed if high energy radiation is applied to initiate polymerization.

Proper and sufficient agitation or stirring is typically required throughout the polymerization in order to produce the spherical and porous beads having the desired size. Thus, the polymerization mixture is agitated to disperse the monomers in the reaction medium by shear action, thereby forming droplets. These droplets are preferably of a size that when transformed into polymer beads, which are spherical, and macroporous, the same will be of the desired size as discussed hereinabove. Various means are available to maintain the proper agitation. When polymerization is conducted in a reactor made of stainless steel, such reactor is preferably fitted with a rotatable shaft having one or more agitator blades. When a round-bottom flask is used as a reactor, an overhead stirrer will agitate the reaction medium. The amount of agitation necessary to obtain the desired results will vary depending upon the particular monomers being polymerized, as well as the particular polymer particle size desired. Therefore, the agitation speed such as the rpm (revolutions per minute) is preferably regulated within certain limits. Polymerization times can vary from about 3 hours to about 24 hours, depending on the reactivity of the monomers.

When polymerization is complete, the ligating anion may be removed from the crosslinked polymer. This is to facilitate exchange for the ion of interest in a more facile manner.

The ion exchange resins thus obtained are preferably in the form of macroporous beads, such as shown in FIG. 1. Although the present resins can swell when contacted with a solvent, swelling is not required to allow access to the interior of the particles through the porous structure. In contrast, gel-type resins do not have a permanent porous structure in the dry state but are preferably swollen by a suitable solvent to allow access to the interior of the particles, and may remain only surface active in a poor solvent. In general, the ion exchange resins of the present invention preferably have an average particle size of from about 50 microns to about 1.5 mm and more preferably from about 300 microns to about 1000 microns. In one embodiment, the ion exchange resins of the present invention preferably have an average particle size distribution in which 90% of the particles have a particle diameter greater than or equal to about 250 microns and less than or equal to about 1000 microns. The average particle size of the IER may be measured by various analytical methods generally known in the art including, for example, ASTM D1921-06.

Embodiments of a device of the present invention provide a cationic ionically imprinted polymer bead that can selectively remove target anions from a fluid such as a liquid. Fluids that contains target compounds and that are suitable for use with the present invention include, but are certainly not limited to, potable water, produced water, mine effluent, mine waste, industrial effluents, settling ponds, evaporation ponds, contaminated natural bodies of water, underground water tables, and the like. A method of the present invention comprises contacting the device containing the cationic IER bead with a fluid for a sufficient amount of time that allows the fluid to penetrate the bead. After the fluid penetrates the bead, the complexing cavities contained in the bead will bind the target compound upon contact, effectively removing the target compound from the liquid.

The cationic IER beads can be utilized in device where a plurality of the same or different beads are employed. In this manner, more than one specific ion can be removed from the fluid to provide a more efficient process. Generally, the fluid can be passed through a column or bed of the beads. A sufficient number of beads is preferably used to remove all of the undesirable inorganic ions that can be removed. The fluid can then be further processed or disposed in an appropriate manner. For example, the target ions can be removed from an aqueous solution, collected, and reused in another application.

According to certain embodiments, the IER of the present invention is used in conjunction with a light source and a detector to form an optical sensor device for detecting a target analyte.

A wide range of suitable detectors can be used according to the present invention. Non-limiting examples of suitable detectors include a spectrophotometer, spectrometer (gas or mass), photomultiplier tube, monochromator equipped with a CCD camera, filters, the naked eye, combinations of two or more thereof, and the like.

A sensor device of the present invention is preferably produced by operatively associating at least one light source and at least one detector with an IER. For the purposes of the present invention, two objects are considered to be "operatively associated" when connected or arranged in a manner such that excitation or luminescent energy produced by one of the objects is capable of being absorbed or detected by the other object. The light source, detector and IER of the present invention, may be operatively associated in any manner such that excitation energy from the light source is transmitted to the IER and absorbed by the complex, such as dicyanoaurate, and the luminescent energy produced by the excited complex is transmitted to, and detected by, the detector. In addition, the components of the present sensor devices may be connected or arranged with or in any suitable medium through which excitation or luminescent energy can be transmitted. Examples of suitable media include air, optical devices, such as films or fibers, and combinations of two or more thereof.

According to certain embodiments, the light source, IER and detector are associated through optical fibers to provide a fiber optic sensor device. In certain embodiments, the fiber optic sensor device for detecting the presence of at least one analyte (such as a cyanide metal complex) in a sample according to the present invention comprises: at least one optical fiber having a proximal end and a distal end for transmitting light energy, the proximal end being disposed within a probe housing, a cationic molecularly imprinted polymer bead being associated with the distal end of the optical fiber, wherein the bead is capable of chemically binding with the analyte, a light source for generating excitation energy, the light source being operatively associated with the optical fiber such that the excitation energy passes through the optical fiber means to the IER, and a detector operatively associated with the optical fiber for detecting luminescent energy generated by the bead.

In some embodiments the device employs a modulated light emitting diode (LED) for excitation and a small photosensor module for detection, with the output going to a microprocessor controlled grated integrator. In addition, an optical multiplex switch may be incorporated into the design so that many sensors can be coupled to one control system, which will allow monitoring of the effluent of an ion exchange column.

In use, a target analyte, if present, binds to the plurality of complexing containing cationic ligands in the IER beads causing the beads to luminesce differently under appropriate excitation, for example by shifting color. Light from the light source means propagates along the optical fiber to its distal end where it undergoes a change caused by interaction with the beads. The modified light returns along the same or another fiber to the detection means which interprets the returned light signal. Detection is based on the change that occurs in the bead's luminescence spectrum when dicyanonaurate, for example, binds to the plurality of complexing containing cationic ligands.

Figure 2:
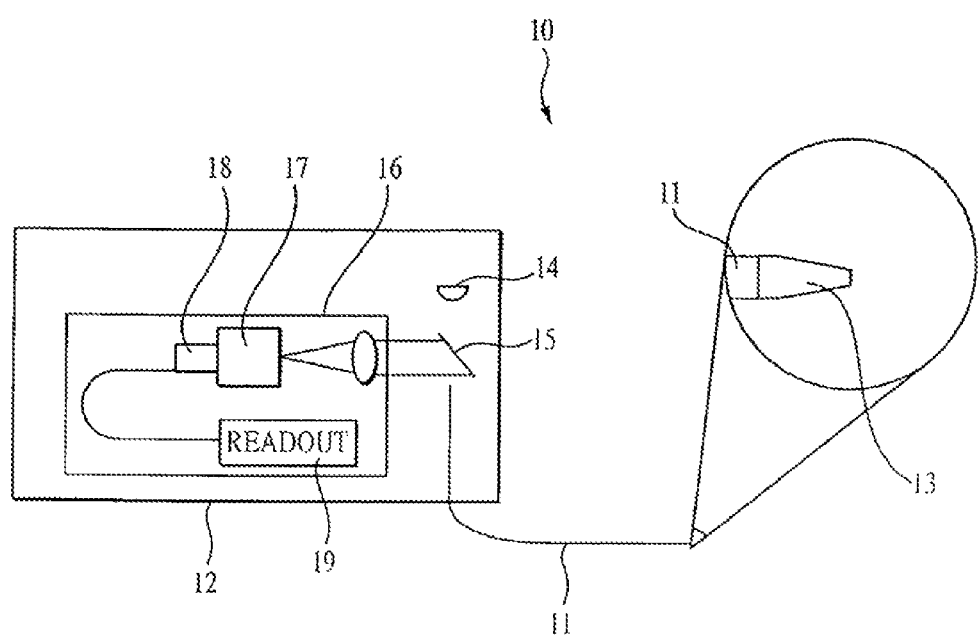
FIG. 2 is an illustration of a sensor device in accordance with the present invention.

FIG. 2 illustrates an exemplary fiber optic portable sensor device according to embodiments of the present invention. Sensor device 10 comprises optical fiber 11 having a proximal end disposed within sensor housing 12 and a distal end associated with a housing 13 containing a cationic molecularly imprinted polymer bead. Alternatively, the fiber can be inserted, for example, in the effluent piping of a bed of beads. Light source 14 preferably comprises a blue LED diode from which light in the blue range of the spectrum is emitted. The light is emitted through dichroic mirror 15 to the proximal end of fiber 11 through which the light energy is transmitted to the plurality of complexing containing cationic ligands in the molecularly imprinted polymer bead. Any luminescence generated by the bead travels back through fiber 11 and is reflected off dichroic mirror 15 to detector 16, which preferably comprises filter 17, photodiode 18, and readout 19. While the exemplary device shown in FIG. 2 comprises a single housing for the detector and light source only, any suitable combination of one or more of the light source, detector, and/or IER can be housed within one or more device housings according to the present invention.

EXAMPLES

The following examples are provided to enable one skilled in the art to practice the invention and are merely illustrative of the invention. The examples should not be read as limiting the scope of the invention as defined in the claims. All chemicals were purchased from Sigma-Aldrich Chemical Company, unless otherwise noted.

Example 1: Preparation of Dicyanoaurate and Dicyanoargentate Selective Beads

Preparation of the ligand N-(4-vinylbenzyl)-N,N,N-tripentyl ammonium chloride (VBzTPAC): In a 2-neck round bottom flask, 4-vinylbenzylchloride (7.13 mL) and tri-n-pentyl amine (11.37 g) were mixed together. The resulting solution was degassed, followed by addition of 10 mL of anhydrous acetonitrile.

The solution was heated to reflux for 5.5 h under Ar. Acetonitrile was removed under vacuum, to yield white foam, which was washed with diethyl ether. The resulting white powder was dried under vacuum.

Preparation of N-(4-vinylbenzyl)-N,N,N-tri-n-pentylammonium thiocyanate bead forming monomer: N-(4-vinylbenzyl)-N,N,N-tripentyl ammonium chloride ligand (7.60 g, 20 mmol) as prepared above was dissolved in water (50 mL, pH=10.5, adjusted with hydrated lime). Potassium thiocyanate (2.13 g, 20 mmol) was also dissolved in water (30 mL, pH=10.5, adjusted with hydrated lime) and was added the ligand solution at a rate of 5 mL/min. Immediately, a white precipitate formed and oil slowly settled from solution. The reaction flask was refrigerated overnight. The following day the aqueous phase was decanted, and the residue washed with water (50 ml). The residue was vacuum dried to give oil that became glassy below 0° C., (8.05 g, quantitative yield). The product was unstable towards polymerization and had to be used immediately to form the beads or stabilized with BHT for storage for short periods. NMR (300 MHz, CDCl3) estimated 7.48-7.43 (dd, 4H); 6.72-6.69 (dd, 1H); 5.85-5.80 (d, 1H); 5.40-5.37 (d, 1H); 4.78 (s, 2H); 3.27-3.23 (t, 6H); 1.83-1.82 (p, 6H); 1.40 (m, 12H); 0.93 (t, 9H). FT-IR Diamond, cm−1=2049 (SCN).

Example 2: Preparation of Perchlorate or Organic Anion Selective Beads

Preparation of the ligand N-(4-vinylbenzyl)-N-decyl-N,N-dimethylammonium chloride:Dimethyl decyl amine (9.30 g, 50 mmol) and 4-vinylbenzylchloride (7.63 g, 50 mmol) were added to ether (20 mL) and were allowed to stir for 12 hours. A yellow solid precipitated and it was collected by filtration resulting in 3 g (17% yield). The ether was removed and the remaining solution was allowed to react neat for 24 hours giving a near quantitative yield after washing with ether. 1H-NMR (90 MHz, $CDCl_3$, δ): 7.68-7.38 (dd, 4H); 6.87-6.56 (dd, 1H); 5.89-5.70 (d, 1H); 5.41-5.29 (d, 1H); 5.09 (s, 2H); 3.51 (bs, 2H); 3.31 (s. 6H); 1.81 (bs, 2H) 1.25 (bs, 14H); 0.92-0.81 (t, 3H).

Bead Preparation, 25% crosslinked, 4% N-(4-vinylbenzyl)-N-decyl-N,N-dimethylammonium chloride: An organic phase was prepared by passing styrene (17.5 g, 168 mmol), and divinylbenzene (6.25 g, 48 mmol) were passed through alumina to remove inhibitor. A suspension polymerization solution was prepared by mixing toluene (22 mL), N-(4-vinylbenzyl)-N-decyl-N,N-dimethylammonium chloride (1.00, 1.8 mmol), 2-ethyl-1-hexanol (3 mL), 1-dodecanethiol (1.25 g, 6.2 mmol) and AIBN (0.250 g, 1.5 mmol). The organic phase was added to the suspension polymerization solution 1 (450 mL) in a 1000 mL reaction bottom fitted with a reaction top and mechanical stirrer. Nitrogen was bubbled through the solution for 10 minutes before heating to 80° C. for 5 hours, while stirring at 300 rpm with a pivot paddle (shaft length 50 cm; 0.7 cm diameter; impeller is 5.0 cm wide). Upon completion of the polymerization, the mixture was diluted with water (550 mL) and allowed to cool. The supernatant was decanted (100 mL reserved for ICP-OES analysis) and the beads were diluted and decanted two more times with water (600 mL). The beads were filtered, washed with water (250 mL), methanol (250 mL), acetone (250 mL), and ether (250 mL). The beads were vacuum dried for at least 4 hours.

Although the invention has been described in detail with particular reference to the disclosed embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. A macroporous ion exchange resin polymer bead comprising:
   a plurality of cationic ligands selective for a specific univalent ion, the ligands co-polymerized with a non-complexing monomer and a crosslinker;
   wherein the bead does not comprise the univalent ion;
   wherein each ligand comprises a coordination site supplying the appropriate charge for the univalent ion; and
   wherein the ligands are sufficiently separated to minimize binding of polyvalent ions to the bead.

2. The bead of claim 1 wherein the monomer comprises styrene and the crosslinker comprises divinyl benzene.

3. The bead of claim 1 wherein the ligand is monodentate.

4. The bead of claim 1 comprising a number of ligands to substantially maximize a binding capacity of the bead to the univalent ion while maintaining spatial separation to minimize cooperative effects between ligands.

5. The bead of claim 1 wherein the ligand is selected from the group consisting of cationic oxygen containing heterocyclics, cationic nitrogen containing heterocyclics, cationic sulfur containing heterocyclics, cationic phosphorous containing heterocyclics, ammonium salts, phosphonium salts, acylinium salts, metallocenium salts, amidinium salts, imminium salts, trityl salts, 4-vinylbenzyl-N,N,N-tripentylammonium, 4-vinylbenzyl-N,N-dimethyl-N-hexylammonium, N,N-dimethyl N-heptylammonium, and 4-vinylbenzyl-N,N-dimethyl-N-decylammonium.

6. The bead of claim 1 wherein the univalent ion is selected from the group consisting of monatomic univalent anions, polyatomic univalent anions, halides, fluoride, chloride, bromide, iodide, univalent oxyanions, perbromate, periodate, permanganate, pertechnetate, nitrite, nitrate, perchlorate, cyanide, cyanate, thiocyanate, organic anions, benzoate, acetate, precious metal cyanide complexes, dicyanoaurate, and dicyanoargentate.

7. The bead of claim 1 wherein the plurality of ligands are specific for a luminescent univalent ion is luminescent.

8. A method for extracting univalent ions from a liquid, the method comprising:

flowing the liquid past a plurality of the beads of claim 1;

maintaining contact between the liquid and the beads sufficiently long for the liquid to substantially penetrate the beads; and binding the univalent ions to the ligands.

9. The method of claim 8 wherein the plurality of beads is in the form of a bed or column.

10. The method of claim 8 wherein the liquid comprises an aqueous solution, potable water, produced water, mine effluent, mine waste, industrial effluent, a settling pond, an evaporation pond, a contaminated natural body of water, or an underground water table.

11. The method of claim 8 further comprising:

shining light on the beads;

luminescing the univalent ions bound to the beads; and measuring a characteristic of the luminescence.

12. The method of claim 11 wherein the characteristic is intensity or wavelength.

13. The method of claim 11 further comprising determining when the plurality of beads is saturated with bound univalent ions.

14. The method of claim 8 wherein the plurality of beads have an average size between approximately 50 microns and approximately 1.5 mm.

15. The method of claim 14 wherein the plurality of beads have an average size between approximately 300 microns and approximately 1000 microns.

* * * * *

UNITED STATES PATENT AND TRADEMARK OFFICE
CERTIFICATE OF CORRECTION

PATENT NO. : 10,252,259 B2
APPLICATION NO. : 15/172095
DATED : April 9, 2019
INVENTOR(S) : George M Murray Page 1 of 1

It is certified that error appears in the above-identified patent and that said Letters Patent is hereby corrected as shown below:

In the Claims

Column 11, Line 26, cancel the text beginning with "7. The bead of claim 1," to and ending with "is luminescent." in Column 11, Line 27, and insert the following claim:
--7. The bead of claim 1 wherein the plurality of ligands are specific for a luminescent univalent ion.--

Signed and Sealed this
Twenty-fourth Day of September, 2019

Andrei Iancu
*Director of the United States Patent and Trademark Office*